United States Patent [19]

Wagle et al.

[11] Patent Number: 5,316,775
[45] Date of Patent: May 31, 1994

[54] METHOD OF TREATING HEPATITIS B INFECTION

[75] Inventors: Sudhakar S. Wagle, Mequon, Wis.; Thomas Steinbach, Houston, Tex.; Carl H. Lawyer, Mequon, Wis.; William J. Hermann, Jr., Sealy, Tex.; Ali A. S. Gawish, Mequon, Wis.

[73] Assignee: Kremers-Urban Company, Mequon, Wis.

[21] Appl. No.: 49,511

[22] Filed: Apr. 19, 1993

Related U.S. Application Data

[63] Continuation-in-part of Ser. No. 803,844, Dec. 4, 1991, and a continuation-in-part of Ser. No. 780,084, Oct. 15, 1991, abandoned, said Ser. No. 803,844, is a continuation-in-part of Ser. No. 728,267, Jul. 11, 1991, abandoned, which is a continuation of Ser. No. 228,364, Aug. 4, 1988, Pat. No. 5,055,296, said Ser. No. 780,084, is a continuation-in-part of Ser. No. 728,267, Jul. 11, 1991, abandoned, which is a continuation of Ser. No. 228,364, Aug. 4, 1988, Pat. No. 5,055,296.

[51] Int. Cl.$^5$ ............................................ A61K 35/407
[52] U.S. Cl. ........................................ 424/553; 514/2; 514/21; 514/893; 514/894
[58] Field of Search ...................... 424/553; 514/2, 21, 514/893, 894

[56] References Cited

U.S. PATENT DOCUMENTS

| | | | |
|---|---|---|---|
| 3,778,510 | 12/1973 | Blonde | 424/553 |
| 4,148,788 | 4/1979 | Wang | 530/324 |
| 4,420,398 | 12/1983 | Castino | 210/641 |
| 4,426,324 | 1/1984 | Meienhofer | 530/301 |
| 4,428,938 | 1/1984 | Kisfaludy | 514/17 |
| 4,464,355 | 8/1984 | Fabricius | 424/85.2 |
| 4,468,379 | 8/1984 | Gottlieb | 424/534 |
| 4,537,878 | 8/1985 | Plotnikoff | 574/2 |
| 4,595,588 | 6/1986 | Baron | 424/89 |
| 4,595,780 | 6/1986 | Ogata | 564/79 |
| 4,596,798 | 6/1986 | Shipman, Jr. | 514/183 |
| 4,598,095 | 7/1986 | Nishimura | 514/632 |
| 4,602,037 | 7/1986 | Scherm | 514/512 |
| 4,603,122 | 7/1986 | Blough | 514/23 |
| 4,603,219 | 7/1986 | Verheyden | 560/255 |
| 4,604,404 | 8/1986 | Munson, Jr. | 514/494 |
| 4,605,658 | 8/1986 | Holy | 514/261 |
| 4,605,659 | 8/1986 | Verheyden | 514/262 |
| 4,606,917 | 8/1986 | Eppstein | 424/85.6 |
| 4,609,661 | 9/1986 | Verheyden | 514/262 |
| 4,609,662 | 9/1986 | Krenitsky | 514/262 |
| 4,612,314 | 9/1986 | Verheyden | 514/261 |
| 4,614,651 | 9/1986 | Jarvis, Jr. | 424/85.4 |
| 4,614,731 | 9/1986 | Horecker | 514/12 |
| 4,617,304 | 10/1986 | Ashton | 514/261 |
| 4,621,140 | 11/1986 | Verheyden | 544/276 |
| 4,622,430 | 11/1986 | Dekker | 564/458 |
| 4,625,026 | 11/1986 | Kim | 544/249 |
| 4,626,524 | 12/1986 | Server | 514/13 |
| 4,628,063 | 12/1986 | Haines | 514/626 |
| 4,629,811 | 12/1986 | Dominianni | 564/99 |
| 4,631,149 | 12/1986 | Rinehart, Jr. | 540/546 |

(List continued on next page.)

FOREIGN PATENT DOCUMENTS

357958 3/1990 European Pat. Off. .

OTHER PUBLICATIONS

Bush et al., "Muraceins–Muramyl Peptides Produced by Nocardia Oriental is As Angiotensin–Converting Enzyme Inhibitors: I. Taxonomy, Fermentation and Biological Properties," *J. Antibiotics* 37(4), 330–335 (1984)

(List continued on next page.)

*Primary Examiner*—Douglas W. Robinson
*Assistant Examiner*—Jean C. Witz
*Attorney, Agent, or Firm*—Tilton, Fallon, Lungmus & Chestnut

[57] ABSTRACT

A therapeutic method for treating hepatitis B infection. The method comprises administering a therapeutically-effective amount of a mammalian liver extract, the extract being characterized by being heat stable, insoluble in acetone and soluble in water, peptide or peptide fragment selected from the groups consisting of Sequence Identification Numbers 1-9.

5 Claims, 12 Drawing Sheets

U.S. PATENT DOCUMENTS

| | | | |
|---|---|---|---|
| 4,644,055 | 2/1987 | Brunelle | 528/371 |
| 4,668,660 | 5/1987 | Paessens | 514/383 |
| 4,670,437 | 6/1987 | Abdulla | 514/247 |
| 4,699,898 | 10/1987 | Gottlieb | 514/18 |
| 4,708,818 | 11/1987 | Montagnier | 435/5 |
| 4,710,380 | 12/1987 | Gottlieb | 424/534 |

OTHER PUBLICATIONS

Chomczynski, et al., "Single-Step Method of RNA Isolation by Acid Guanidinium Thiocyanate-Phenol-Chloroform Extraction," *Anal. Biochem.* 162:156–159 (1987).

Jacobson, A. "Purification and Fractionation of Poly(A)+ RNA," *Meth. Enzymology* 152:254–261 (1987).

Korba et al., "Use of a Standardized Cell Culture Assay to Assess Activities of Nucleoside Analogs Against Hepatitis B Virus Replication," *Antiviral Res.* 19:55–70 (1992).

Korba et al., "A Cell Culture Assay For Compounds Which Inhibit Hepatitis B Virus Replication," *Antiviral Res.* 15:217–228 (1991).

Mierendorf et al. "Direct Sequencing of Denatured Plasmid DNA," *Meth. Enzymol.* 152:556–562 (1987).

Andrews et al. *JAMA*, 146, 1107 (1951).

Barksdale, *South. Med. Jour.*, 50, 1524 (1957).

Barksdale, et al., *Virginia Medical Monthly*, 81, 321 (1954).

Barrock, *Medical Times*, 1, (Aug. 1958).

Boreen, *Minnesota Medicine*, 25, 276 (1942).

Burks, Jr., *Journal of the Louisiana Medical Society*, 106, 92 (1954).

Burks, Jr. and Knox, *Archives of Dermatology and Syphilology*, 70 508 (1954).

Center for Disease Control, Dept. Health and Human Services, Chronic *Fatigue Syndrome*, Mar. 22, 1988.

Chase, *Wall Street Journal*, Apr. 28, 1988, at 14, at col. 1.

Gaskell, *Brit. Med. J.*, p. 1037 (Jun. 11, 1949).

Gathings, *Am. J. Surgery*, 88, 429 (1954).

Gladner, Ann. N.Y. Aca. Sci 47.

Harris, et al., *Oral Surgery*, 7, 239 (1954).

Hellinger, et al., *JAMA*, 260, 971 (Aug. 19, 1988).

Heywood, *Clinical Medicine*, 3, 425 (1956).

Hjerten, *Archives of Biochemistry and Biophysics*, Suppl. 1, 147 (1962).

Hjerten and Mosbach, *Analytical Biochemistry*, 3, 109 (1962).

Holtman, *Oral Surgery*, 7, 12 (1954).

Judge, *Proc. Soc. Exptl. Biol. Med.*, 123, 199 (1966).

Kozelka and Marshall, *Clinical Medicine*, 3, 245 (1956).

Kutapressin-Drug Package Insert, Kremers-Urban.

Li, et al., *Nature*, 219, 1163 (Sep. 14, 1968).

Li, et al., *Proc. Soc. Exptl. Biol. Med.*, 114, 504 (1963).

Li, et al., *Proc. Soc. Exptl. Biol. Med.*, 109, 534 (1962).

Li, et al., *J. Nat'l Cancer Inst.*, 41, 1249 (Nov. 1968).

Li, et al., *Ann. N.Y. Acad. Sci.*, 130, 374 (1965).

Lichtenstein and Stillians, Arch. Dermatology and Syphilology, 45, 595 (1942).

Lubowe, *Clinical Medicine*, 59, 8 (1952).

Marshall, et al., *Am. J. Surgery*, 90, 47 (1955).

Marshall, Maryland State Med. J., (Jun. 1960).

Marshall, *Am. J. Surgery*, 84(6), 675 (1952).

Marshall, and Schadeberg, *Wisconsin Medical Journal*, 49, 369 (1950).

Marshall and Schadeberg, *Indian J. Veneral Diseases*, 16, 89 (1950).

Marshall, *J.M.A. Alabama*, 13, 255 (1944).

Marshall, *Mississippi Valley Med. J.*, 61, 172 (1939).

Marshall, *Med. World*, 57, 101 (1939).

Marshall, *Northwest Medicine*, 38, 467 (1939).

Marshall, *J. Invest. Derm.*, 2, 105 (1939).

Marshall, *A. J. Surgery*, 448 (Oct. 1951.

Marshall, *Medical Times*, 70, 222 (1951).

Marshall, *Indian J. Veneral Diseases and Dermatology*, 20, 99 (1954).

Marshall, *The Journal-Lancet*, 60, 117 (1940).

Marshall, *Minnesota Medicien*, 25, 796 (1942).

Marshall, *Arizone Medicine*, 14(1), 11 (1957).

Marshall, *Mississippi Valley Med. J.*, 76, 199 (1954).

Mitchell-Heggs, *Brit. Med. J.*, 2, 1079 (1951).

Montefiori, et al., *J. Clin. Micro.*, 26, 231 (Feb. 1988).

Montefiori and Mitchell, *Proc. Nat'l Acad. Sci U.S.A.*, 84(9), 2985 (May 1987).

National Formulary, vol. XII, p. 222.

Nierman, *Journal of the Indiana State Medical Association*, 45, 497 (1952).

Osbahr, et al., *Biochim. Biophys. Acta.*, 86, 535 (1964).

Pensky and Goldberg, *The Journal-Lancet*, 75(11), 490 (Nov. 1955).

(List continued on next page.)

OTHER PUBLICATIONS

Pensky and Goldberg, *New York State Journal of Medicine*, 53, 2238 (1953).
*Pharmacopeia of the United States*, 15, 379.
Pollner, *Medical World News*, 35 (Jun. 13, 1988).
Poole, *South Med. J.*, 50, 207 (1957).
Ruggieri, *Science*, 194, 491 (1976).
Schmeer and Huala, *Ann. N.Y. Acad. Sci.*, 118, 605 (1965).
Schmeer, *Science*, 144, 413 (1964).
Smith, *HIV and Other Highly Pathogenic Viruses*, Academic Press, Inc. (1988).
Stillians, *Mississippi Valley Medical Journal*, 64, 135 (1942).
Stokes and Sternberg, *Archives of Dermatology and Syphilology*, 40, 345 (1939).
Sutton, *Archives of Dermatology and Syphilology*, 18, 887 (1928).
Tewksbury and Stahmann, *Arch. Biochem. Biophys. (U.S.)*, 112, 453 (1965).
Tewksbury, *Archives Int'l de Pharmacodynamic et de Therapie*, 173, 426 (1968).
Tewksbury, *Dissertation Abstracts International–Part II*, 25-04, 2214 (1964).
Walters, *Ohio State Medical Journal*, 44, 697 (1948).

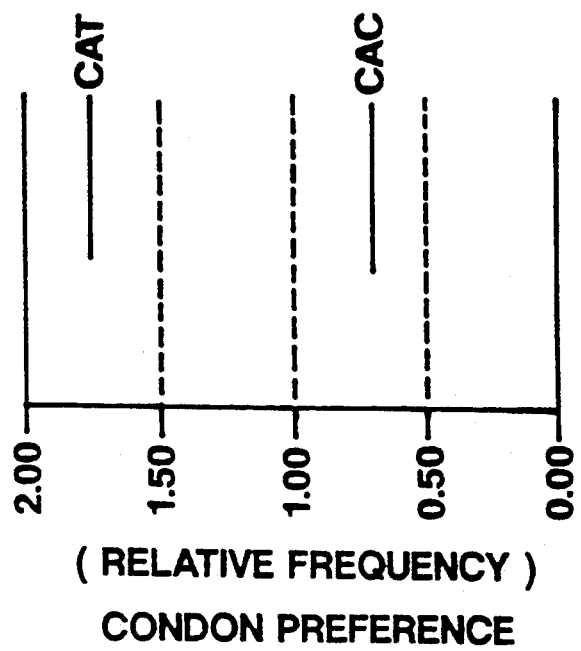
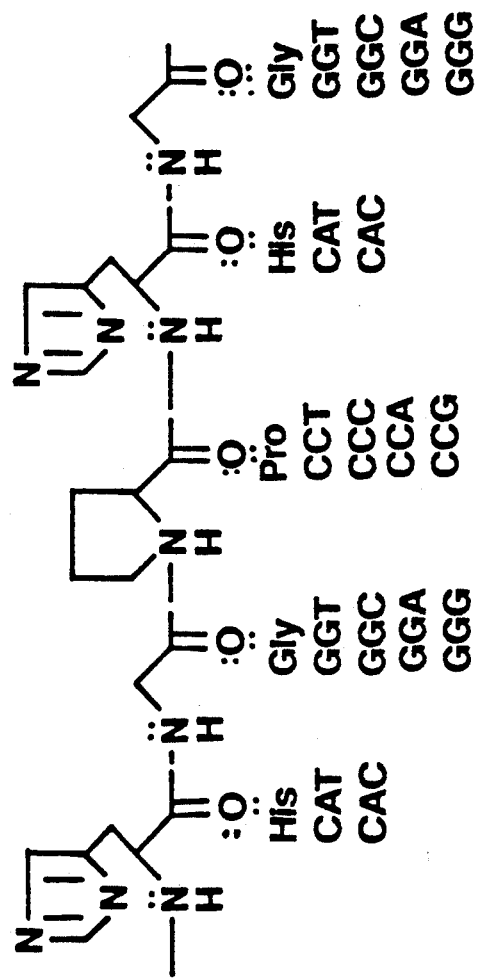
Fig. 1B
Fig. 1A

Fig. 2A

KU214 and 215 peptide:
```
5'GGGCCGCATGGGCAAAGTATTATGCTCGGCCTGAACAGTGTATTTTATCCAAGTGCAATAATACGTCAAGCTGCACCTTTT
3'CCCGGCGTACCCGTTTCATAATACGAGCCGGACTTGTCACATAAAATAGGTTCACGTTATTATGCAGTTCGACGTGGAAAA
TTTGACTTCTGCTGG    CTATAAATGTGCATTTATCAGAAGTTGATGTAAACACTATTCTAGTACTGTTCCTTCATCTAGA
AAACTGAAGACGACC···GATATTTACACGTAAATAGTCTTCAACTACATTTGTGATAAGATCATGACAAGGAAGTAGATCT
TTGATCAATTTTAATTAAAATTAAGCACTAAAAAAAAAAAAAAAA    CTATCGATTCTGGAACCTTCAGAGG3'
AACTAGTTAAAATTAATTTTAATTCGTGATTTTTTTTTTTTTTTT···GATAGCTAAGACCTTGGAAGTCTCC5'
```

5'CATGGICCICATGGI3'  PRIMER#1

5'CCTCTGAAGGTTCCAGAATCGATAG3'  PRIMER#2   (CLONTECH UNI-AMP PRIMER)

Cycle 1    | denature, re-anneal
               V

```
5'GGGCCGCATGGGCAAAGTATTATGCTCGGCCTGAACAGTGTATTTTATCCAAGTGCAATAATACGTCAAGCTGCACCTTT
TTTTGACTTCTGCTGG...CTATAAATGTGCATTTATCAGAAGTTGATGTAAACACTATTCTAGTACTGTTCCTTCATCTAG
ATTGATCAATTTTAATTAAAATTAAGCACTAAAAAAAAAAAAAAAA...CTATCGATTCTGGAACCTTCAGAGG3'
```
            PRIMER#2 EXTENDS  ←------------3'GATAGCTAAGACCTTGGAAGTCTCC5'

5'CATGGICCICATGGI3' PRIMER#1 -------------> EXTENDS

```
3'___CCCGGCGTACCCGTTTCATAATACGAGCCGGACTTGTCACATAAAATAGGTTCACGTTATTATGCAGTTCGACGTGG
AAAAAAACTGAAGACGACCGATATTTACACGTAAATAGTCTTCAACTACATTTGTGATAAGATCATGACAAGGAAGTAGATC
TAACTAGTTAAAATTAATTTTAATTCGTGATTTTTTTTTTTTTTTTTGATAGCTAAGACCTTGGAAGTCTCC5'
```

Cycle 1    | Polymerase, dNTPs
               V

```
5'GGGCCGCATGGGCAAAGTATTATGCTCGGCCTGAACAGTGTATTTTATCCAAGTGCAATAATACGTCAAGCTGCACCTTTT
3'CCCGGCGTACCCGTTTCATAATACGAGCCGGACTTGTCACATAAAATAGGTTCACGTTATTATGCAGTTCGACGTGGAAAA
TTTGACTTCTGCTGG    CTATAAATGTGCATTTATCAGAAGTTGATGTAAACACTATTCTAGTACTGTTCCTTCATCTAGA
AAACTGAAGACGACC···GATATTTACACGTAAATAGTCTTCAACTACATTTGTGATAAGATCATGACAAGGAAGTAGATCT
TTGATCAATTTTAATTAAAATTAAGCACTAAAAAAAAAAAAAAAA    CTATCGATTCTGGAACCTTCAGAGG3'
AACTAGTTAAAATTAATTTTAATTCGTGATTTTTTTTTTTTTTTT···GATAGCTAAGACCTTGGAAGTCTCC5'
```

```
5'GGGCCGCATGGGCAAAGTATTATGCTCGGCCTGAACAGTGTATTTTATCCAAGTGCAATAATACGTCAAGCTGCACCTTTT
3'CCCGGCGTACCCGTTTCATAATACGAGCCGGACTTGTCACATAAAATAGGTTCACGTTATTATGCAGTTCGACGTGGAAAA
TTTGACTTCTGCTGG    CTATAAATGTGCATTTATCAGAAGTTGATGTAAACACTATTCTAGTACTGTTCCTTCATCTAGA
AAACTGAAGACGACC···GATATTTACACGTAAATAGTCTTCAACTACATTTGTGATAAGATCATGACAAGGAAGTAGATCT
TTGATCAATTTTAATTAAAATTAAGCACTAAAAAAAAAAAAAAAA    CTATCGATTCTGGAACCTTCAGAGG3'
AACTAGTTAAAATTAATTTTAATTCGTGATTTTTTTTTTTTTTTT···GATAGCTAAGACCTTGGAAGTCTCC5'
```

Cycle 2    | denature, re-anneal
               V

```
5'GGGCCGCATGGGCAAAGTATTATGCTCGGCCTGAACAGTGTATTTTATCCAAGTGCAATAATACGTCAAGCTGCACCTTT
TTTTGACTTCTGCTGG...CTATAAATGTGCATTTATCAGAAGTTGATGTAAACACTATTCTAGTACTGTTCCTTCATCTAG
ATTGATCAATTTTAATTAAAATTAAGCACTAAAAAAAAAAAAAAAA...CTATCGATTCTGGAACCTTCAGAGG3'
```
            PRIMER#2 EXTENDS  ←------------3'GATAGCTAAGACCTTGGAAGTCTCC5

5'CATGGICCICATGGI3' PRIMER#1 -------------> EXTENDS

```
3'___CCCGGCGTACCCGTTTCATAATACGAGCCGGACTTGTCACATAAAATAGGTTCACGTTATTATGCAGTTCGACGTGG
AAAAAAACTGAAGACGACCGATATTTACACGTAAATAGTCTTCAACTACATTTGTGATAAGATCATGACAAGGAAGTAGATC
TAACTAGTTAAAATTAATTTTAATTCGTGATTTTTTTTTTTTTTTTTGATAGCTAAGACCTTGGAAGTCTCC5'
5'GGGCCGCATGGGCAAAGTATTATGCTCGGCCTGAACAGTGTATTTTATCCAAGTGCAATAATACGTCAAGCTGCACCTTT
```

Fig. 2A (cont.)

```
5'GGGCCGCATGGGCAAAGTATTATGCTCGGCCTGAACAGTGTATTTTATCCAAGTGCAATAATACGTCAAGCTGCACCTTT
3'CCCGGCGTACCCGTTTCATAATACGAGCCGGACTTGTCACATAAAATAGGTTCACGTTATTATGCAGTTCGACGTGGAAAA
TTTGACTTCTGCTGG   CTATAAATGTGCATTTATCAGAAGTGATGTAAACACTATTCTAGTACTGTTCCTTCATCTAGA
AACTGAAGACGACC...GATATTTACACGTAAATAGTCTTCAACTACATTGTGATAAGATCATGACAAGGAAGTAGATCT
TTGATCAATTTTAATTAAAATTAAGCACTAAAAAAAAAAA    CTATCGATTCTGGAACCTTCAGAGG3'
AACTAGTTAATTAATTTAATTCGTGATTTTTTTTTTTT...GATAGCTAAGACCTTGGAAGTCTCC5'

Cycle 2  | denature, re-anneal
                             v

5'GGGCCGCATGGGCAAAGTATTATGCTCGGCCTGAACAGTGTATTTTATCCAAGTGCAATAATACGTCAAGCTGCACCTTT
3'CCCGGCGTACCCGTTTCATAATACGAGCCGGACTTGTCACATAAAATAGGTTCACGTTATTATGCAGTTCGACGTGGAAAA
TTTGACTTCTGCTGG   CTATAAATGTGCATTTATCAGAAGTGATGTAAACACTATTCTAGTACTGTTCCTTCATCTAGA
AACTGAAGACGACC...GATATTTACACGTAAATAGTCTTCAACTACATTGTGATAAGATCATGACAAGGAAGTAGATCT
TTGATCAATTTTAATTAAAATTAAGCACTAAAAAAAAAAA    CTATCGATTCTGGAACCTTCAGAGG3'
AACTAGTTAATTAATTTAATTCGTGATTTTTTTTTTTT...GATAGCTAAGACCTTGGAAGTCTCC5'

PRIMER-2 EXTENDS <-------     ------> PRIMER-1 EXTENDS

5' CATGGTCCCTCATGGI3' PRIMER-1
   ::::::::::::::::
3' ....CCCGGGCGTACCCGTTTCATAATACGAGCCGGACTTGTCACATAAATAGGTTCACGTTATTATGCAGTTCGACGTGG
       AAAAAACTGAAGACGACCGATATTTACACGTAAATAGTCTTCAACTACATTTGTGATAAGACTTGGAAGTCTCC5'
       TAACTAGTTAATTAATTTAATTCGTGATTTTTTTTTTTTTGATAGCTAAGACCTTGGAAGTCTCC5'
       ATTGATCAATTTAAAATTAAGCACTAAAAAAAA...CTATCGATTCTGGAACCTTCAGAGG3'
                                                                  :::::::::::::::::
                                                           3' GATAGCTAAGACCTTGGAAGTCTCC5'
5' GGGCCGCATGGGCAAAGTATTATGCTCGGCCTGAACAGTGTATTTTATCCAAGTGCAATAATACGTCAAGCTGCACCTTT
```

Fig. 2B

```
TTTGACTTCTGCTGG...CTATAAATGTGCATTTATCAGAAGTTGATGTAAACACTATTCTAGTACTGTTCCTTCATCTAG
ATTGATCAATTTAATTAAGCACTAAAAAAAAAAA...CTATCGATTCTGGAACCTTCAGAGG3'
            PRIMER-2 EXTENDS <--------                   ::::::::::::
                                                    3'GATAGCTAAGACCTTGGAAGTCTCC5'

5'CATGGICCICATGGI3' PRIMER-1 --------> EXTENDS
   ::::::::::
3'   CCCGGGCGTACCCGTTTCATAATACGAGCCGGACTTGTCACGTTATTATGCAGTTCGACGTGG
AAAAAACTGAAGACGACGATATTTACACGTAAATAGTCTTCAACTACATTGTGATAAGATCATGACAAGGAAGTAGATC
TAACTAGTTAAAATTAATTTAATTCGTGATTTTTTTTTTTTGATAGCTAAGACCTTGGAAGTCTCC5'
                                    |
                          Cycle 2    | Polymerase, dNTPs
                                    V 5'GGGCCCGCATGGGCAAAGTATTATGCTCGGCCTGAACAGTGTATTTATCCAAGTGCAATAATACGTCAAGCTGCACCTTTT
3'CCCGGGCGTACCCGTTTCATAATACGAGCCGGACTTGTCACATAAATAGGTTCACGTTATTATGCAGTTCGACGTGGAAAA
TTTGACTTCTGCTGG  CTATAAATGTGCATTTATCAGAAGTTGATGTAAACACTATTCTAGTACTGTTCCTTCATCTAGA
AAACTGAAGACGACC...GATATTTACACGTAAATAGTCTTCAACTACATTGTGATAAGATCATGACAAGGAAGTAGATCT
TTGATCAATTTAATTAAGCACTAAAAAAAAAAA  CTATCGATTCTGGAACCTTCAGAGG3
AACTAGTTAAATTAATTTTAATTCGTGATTTTTTTTTT...GATAGCTAAGACCTTGGAAGTCTCC5
```

Fig. 2B (cont.)

```
5'GGGCCGCATGGGCAAGTATTATGCTCGGCCTGAACAGTGTATTTTATCCAAGTGCAATAATACGTCAAGCTGCACCTTTT
3'CCCGGGCGTACCCGTTCATAATACGAGCCGGACTTGTCACATAAAATAGGTTCACGTTATTATGCAGTTCGACGTGGAAAA
TTTGACTTCTGCTGG    CTATAAATGTGCATTTATCAGAAGTTGATGTAAACACTATTCTAGTACTGTTCCTTCATCTAGA
AACTGAAGACGACC···GATATTTACACGTAAATAGTCTTCAACTACACATTGTGATAAGATCATGACAAGGAAGTAGATCT
TTGATCAATTTAATTAAAATTAAGCACTAAAAAAAAAAAA         CTATCGATTCTGGAACCTTCAGAGG3'
AACTAGTTAAATTAATTTAATTCGTGATTTTTTTTTTT···GATAGCTAAGACCTTGGAAGTCTCC5'

5'GGGCCGCATGGGCAAGTATTATGCTCGGCCTGAACAGTGTATTTTATCCAAGTGCAATAATACGTCAAGCTGCACCTTTT
3'CCCGGGCGTACCCGTTCATAATACGAGCCGGACTTGTCACATAAAATAGGTTCACGTTATTATGCAGTTCGACGTGGAAAA
TTTGACTTCTGCTGG    CTATAAATGTGCATTTATCAGAAGTTGATGTAAACACTATTCTAGTACTGTTCCTTCATCTAGA
AACTGAAGACGACC···GATATTTACACGTAAATAGTCTTCAACTACACATTGTGATAAGATCATGACAAGGAAGTAGATCT
TTGATCAATTTAATTAAAATTAAGCACTAAAAAAAAAAAA         CTATCGATTCTGGAACCTTCAGAGG3'
AACTAGTTAAATTAATTTAATTCGTGATTTTTTTTTTT···GATAGCTAAGACCTTGGAAGTCTCC5'

5'GGGCCGCATGGGCAAGTATTATGCTCGGCCTGAACAGTGTATTTTATCCAAGTGCAATAATACGTCAAGCTGCACCTTTT
3'CCCGGGCGTACCCGTTCATAATACGAGCCGGACTTGTCACATAAAATAGGTTCACGTTATTATGCAGTTCGACGTGGAAAA
TTTGACTTCTGCTGG    CTATAAATGTGCATTTATCAGAAGTTGATGTAAACACTATTCTAGTACTGTTCCTTCATCTAGA
AACTGAAGACGACC···GATATTTACACGTAAATAGTCTTCAACTACACATTGTGATAAGATCATGACAAGGAAGTAGATCT
TTGATCAATTTAATTAAAATTAAGCACTAAAAAAAAAAAA         CTATCGATTCTGGAACCTTCAGAGG3'
AACTAGTTAAATTAATTTAATTCGTGATTTTTTTTTTT···GATAGCTAAGACCTTGGAAGTCTCC5'
                                      |
                                      v
                                further Cycles
```

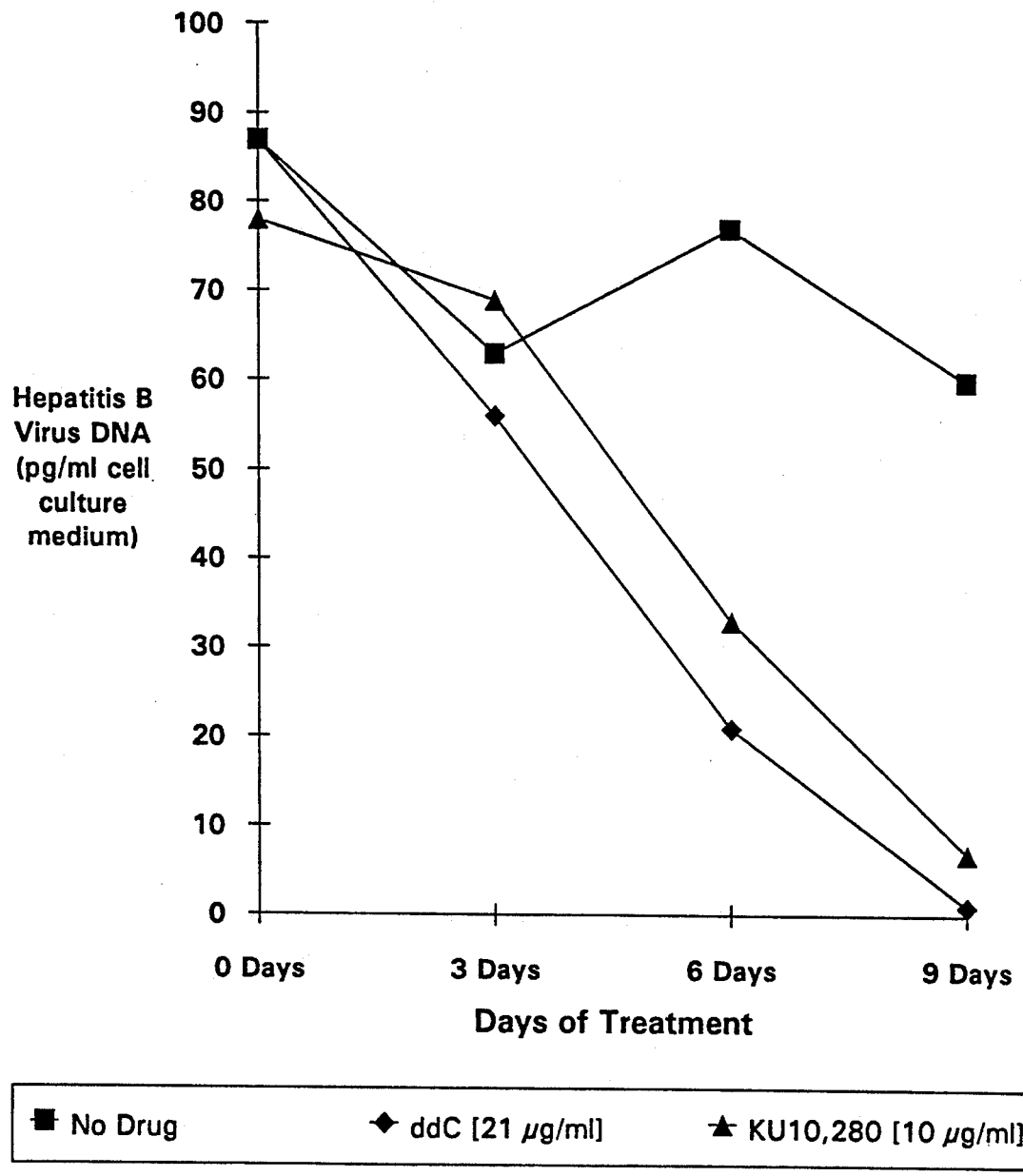

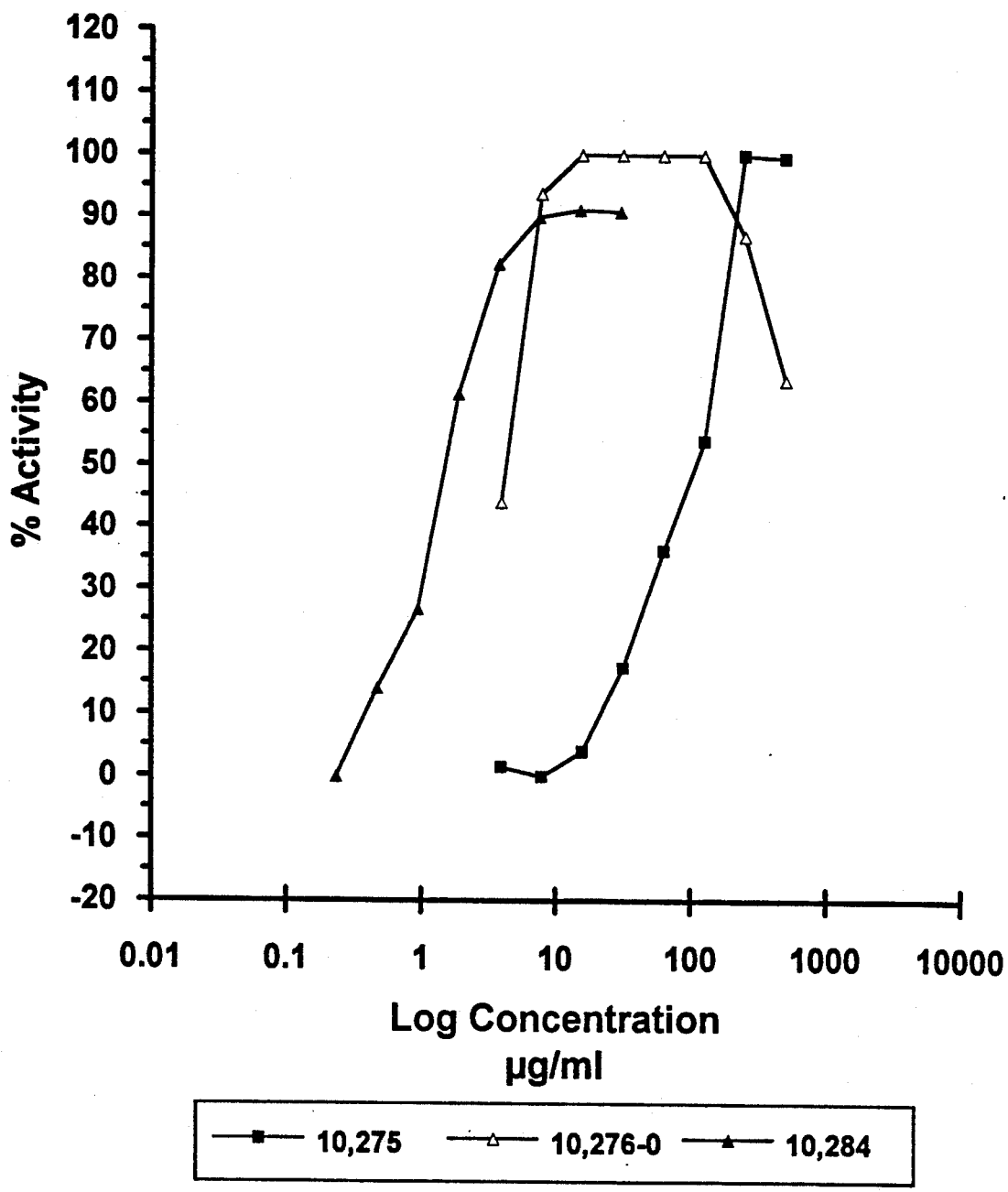

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 32 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:1:

```
Gly  Pro  His  Gly  Gln  Ser  Ile  Met  Leu  Gly  Leu  Asn  Ser  Val  Phe  Tyr
 1               5                        10                       15

Pro  Ser  Ala  Ile  Ile  Arg  Gln  Ala  Ala  Pro  Phe  Phe  Asp  Phe  Cys  Trp
               20                       25                       30
```

( 2 ) INFORMATION FOR SEQ ID NO:2:

( i ) SEQUENCE CHARACTERISTICS:
        ( A ) LENGTH: 96 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

```
GGGCCGCATG  GGCAAAGTAT  TATGCTCGGC  CTGAACAGTG  TATTTTATCC  AAGTGCAATA      60
ATACGTCAAG  CTGCAGCTTT  TTTTGACTTC  TGCTGG                                  96
```

( 2 ) INFORMATION FOR SEQ ID NO:3:

( i ) SEQUENCE CHARACTERISTICS:
        ( A ) LENGTH: 110 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

```
CTATAAATGT  GCATTTATCA  GAAGTTGATG  TAAACACTAT  TCTAGTACTG  TTCCTTCATC      60
TAGATTGATC  AATTTTAATT  AAAATTAAGC  ACTAAAAAAA  AAAAAAAAA                  110
```

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:4:

```
Tyr  Lys  Cys  Ala  Phe  Ile  Arg  Ser
 1                    5
```

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:5:

CTATAAATGT GCATTTATCA GAAGT　　　　　　　　　　　　　　　　　　　　　　　　25

( 2 ) INFORMATION FOR SEQ ID NO:6:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:6:

Ile  Asn  Val  His  Leu  Ser  Glu  Val  Asp  Val  Asn  Thr  Ile  Leu  Val  Leu
1              5                        10                       15

Phe  Leu  His  Leu  Asp
              20

( 2 ) INFORMATION FOR SEQ ID NO:7:

( i ) SEQUENCE CHARACTERISTICS:
        ( A ) LENGTH: 65 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:7:

CTATAAATGT  GCATTTATCA  GAAGTTGATG  TAAACACTAT  TCTAGTACTG  TTCCTTCATC　　60

TAGAT　　　　　　　　　　　　　　　　　　　　　　　　　　　　　　　　　　65

( 2 ) INFORMATION FOR SEQ ID NO:8:

( i ) SEQUENCE CHARACTERISTICS:
        ( A ) LENGTH: 50 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:8:

Gly  Pro  His  Gly  Gln  Ser  Ile  Met  Leu  Gly  Leu  Asn  Ser  Val  Phe  Tyr
1              5                        10                       15

Pro  Ser  Ala  Ile  Ile  Arg  Gln  Ala  Ala  Pro  Phe  Phe  Asp  Phe  Cys  Trp
              20                       25                       30

Xaa  Xaa  Xaa  Xaa  Xaa  Xaa  Xaa  Xaa  Xaa  Xaa  Tyr  Lys  Cys  Ala  Phe  Ile
              35                       40                       45

Arg  Ser
50

( 2 ) INFORMATION FOR SEQ ID NO:9:

( i ) SEQUENCE CHARACTERISTICS:
        ( A ) LENGTH: 63 amino acids
        ( B ) TYPE: amino acid
        ( C ) STRANDEDNESS: unknown ( D ) TOPOLOGY: unknown ( i i ) MOLECULE TYPE: peptide ( x i ) SEQUENCE DESCRIPTION: SEQ ID NO:9:

```
Gly Pro His Gly Gln Ser Ile Met Leu Gly Leu Asn Ser Val Phe Tyr
1               5                   10                  15

Pro Ser Ala Ile Ile Arg Gln Ala Ala Pro Phe Phe Asp Phe Cys Trp
            20                  25              30

Xaa Xaa Xaa Xaa Xaa Xaa Xaa Xaa Xaa Xaa Ile Asn Val His Leu Ser
        35                  40                  45

Glu Val Asp Val Asn Thr Ile Leu Val Leu Phe Leu His Leu Asp
50                  55                  60
```

( 2 ) INFORMATION FOR SEQ ID NO:10:

( i ) SEQUENCE CHARACTERISTICS:
  ( A ) LENGTH: 10 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:10:

```
Xaa Glu Xaa Gly Xaa His Gly Pro His Gly
1               5                   10
```

( 2 ) INFORMATION FOR SEQ ID NO:11:

( i ) SEQUENCE CHARACTERISTICS:
  ( A ) LENGTH: 10 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:11:

```
Xaa Xaa Xaa Gly Thr His Xaa Pro His Gly
1               5                   10
```

( 2 ) INFORMATION FOR SEQ ID NO:12:

( i ) SEQUENCE CHARACTERISTICS:
  ( A ) LENGTH: 15 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:12:

```
Xaa Xaa Xaa Gly Xaa His Gly Xaa His Gly Xaa Xaa Gly Xaa Gln
1               5                   10                  15
```

( 2 ) INFORMATION FOR SEQ ID NO:13:

( i ) SEQUENCE CHARACTERISTICS:
  ( A ) LENGTH: 10 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:13:

```
Ala Glu His Gly Tyr His Gly Pro His Gly
1               5                   10
```

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: modifiedbase
        ( B ) LOCATION: 6
        ( C ) OTHER INFORMATION: /modbase=i ( i x ) FEATURE:
        ( A ) NAME/KEY: modifiedbase
        ( B ) LOCATION: 9
        ( C ) OTHER INFORMATION: /modbase=i ( i x ) FEATURE:
        ( A ) NAME/KEY: modifiedbase
        ( B ) LOCATION: 15
        ( C ) OTHER INFORMATION: /modbase=i ( x i ) SEQUENCE DESCRIPTION: SEQ ID NO:14:

CATGGNCCNC ATGGN

15

METHOD OF TREATING HEPATITIS B INFECTION

BACKGROUND OF THE INVENTION

This application is a continuation-in-part of U.S. Ser. No. 803,844 filed Dec. 4, 1991, pending, which in turn is a continuation in-part of U.S. Ser. No. 07/728,267 filed Jul. 11, 1991, abandoned, which is a continuation of U.S. Ser. No. 07/228,364 filed Aug. 4, 1988, now U.S. Pat. No. 5,055,296. This application is also a continuation-in-part of U.S. Ser. No. 07/780,084 filed Oct. 15, 1991, abandoned, which in turn is a continuation in-part of U.S. Ser. No. 07/728,267 filed Jul. 11, 1991, abandoned, which is a continuation of U.S. Ser. No. 07/228,364 filed Aug. 4, 1988, now U.S. Patent No. 5,055,296.

FIELD OF THE INVENTION

The present invention is directed to a method of treating hepatitis B. infection and to the discovery that a mammalian liver extract that is efficacious in treating such diseases. The present invention is also directed to a method of treating such diseases with this same mammalian liver extract and/or with polypeptides shown in Sequence identification numbers 1-9.

DESCRIPTION OF THE PRIOR ART

Acute hepatitis B causes significant mortality and morbidity and chronic infection with this virus is also associated with hepatocellular carcinoma, chronic active hepatitis and cirrhosis of the liver.

Mammalian liver extract has been used for the treatment of a wide range of infectious and noninfectious dermatologic conditions, including acne vulgaris, *Journal Invest Dermatology*, 2:205-218 (1939); first and second degree burns, *Mississippi Valley Medical Journey*, 76:199 (1954); sunburn, *Clinical Medicine*, 3:245 (1956); poison ivy dermatitis, *Clin. Med.*, 3:425 (1956) and Herpes zoster, *Southern Medical Journal*, 50:1524 (1957). The active principle and mechanism have not been described. Although some medical practitioners have used liver extract for the treatment of dermatologic conditions, it is not regarded as an antiviral or immune modulator agent even for skin therapy.

Mammalian liver extract has been reported to have bradykinin potentiating activity. Tewksbury et al., *Arch. Biochem. Biophys. (U.S.)*, 112, 453 (1965); Tewksbury, *Archives Int'l. de Pharmacodynamie et de Therapie*, 173, 426 (1968); Tewksbury, *Dissertation Abstracts International-Part II*, Vol. 25/04, p. 2214 (1964). Further, one commercially-available liver extract (sold under the trademark KUTAPRESSIN by Kremers-Urban Co., Milwaukee, Wis.) exerts its action, according to product literature, only with respect to tissues that have been injured and when inflammation and edema are present.

In related U.S. Pat. No. 5,055,296, the use of a heat stable acetone-insoluble, water-soluble mammalian liver extract was shown to be effective in the treatment of mammals infected with nondermatologic viruses, in particular, in the treatment of chronic fatigue syndrome. Thus, with this background, the inventors endeavored to discover a method to treat hepatitis B infections.

SUMMARY OF THE INVENTION

The present invention provides a method of treating hepatitis B infection involving administering to a mammal having said disease a therapeutically-effective amount of mammalian liver extract, the extract being characterized by being heat stable, insoluble in acetone and soluble in water. The terminology "heat stable" means that the liver extract does not lose appreciable activity at temperatures at about 100° C. in water over ten minutes. Additionally, this invention relates to a method of treating hepatitis B infection involving administering to a mammal having said disease a therapeutically effective amount of a peptide or peptide fragment selected from the group consisting of Sequence Identification Nos. 1-9.

BRIEF DESCRIPTION OF THE DRAWINGS

FIGS. 1A and 1B show codon bias for His using all pig sequences in GENBANK 66.

FIGS. 2A and 2B illustrate the strategy used for sequencing the active peptide.

FIG. 5B shows anti-virus effect of 10 $\mu$g/ml of active peptide compared to 2.1 $\mu$g/ml 2,3'-dideoxycytosine.

FIG. 6 shows % activity of KU 10,275, 10,276 and 10,284.

DETAILED DESCRIPTION OF THE PRESENTLY PREFERRED EMBODIMENTS

Figure 3:
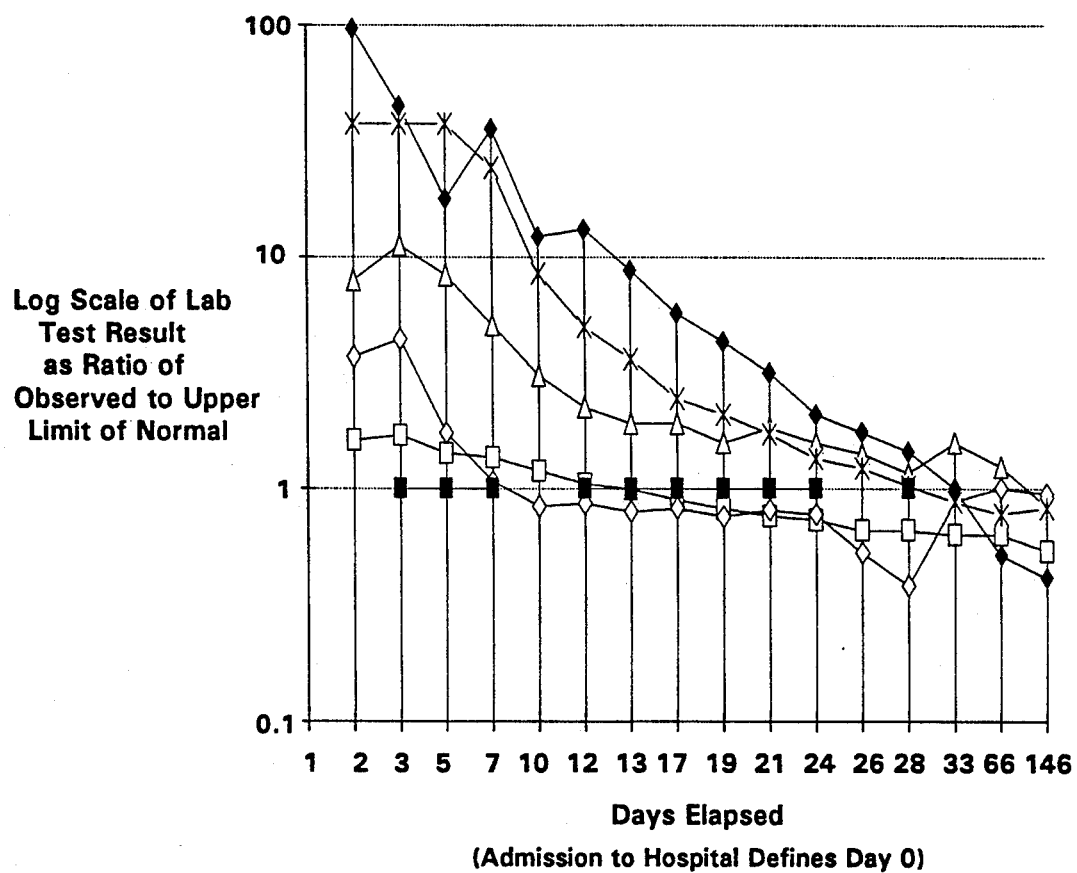
FIG. 3 shows acute hepatitis B patient number 1's liver function data charted during and after administration of KUTAPRESSIN (Kremers-Urban Co.).

The portion of mammalian liver extract that has been discovered to be effective in treating hepatitis B infection is the fraction which is heat stable, insoluble in acetone and soluble in water. The liver extract prepared according to the disclosure herein is free from fatty acids, and vitamins, and specifically is free from vitamin B-12, a vitamin naturally occurring in liver. Additionally, polypeptides have been discovered to be effective in treating hepatitis B infection. Work in progress suggests polysaccharides may be present in KUTAPRESSIN (Kremers-Urban Co.) in the form of proteoglycans and/or glycoproteins. The same liver extract has been used heretofore in treating skin conditions.

PREPARATION OF THE LIVER EXTRACT

The liver extract employed in the present invention is prepared by separating a fraction from mammalian livers, preferably porcine liver. The starting material may be a liver preparation as described in *Pharmacopeia of the United States*, Vol. 15, p. 379 (which describes a boiled liver extract suitable for parenteral use), in *National Formulary*, Vol. XII, p. 222 (which describes an aqueous solution of the thermostable fraction of mammalian liver) or in *National Formulary*, Vol. XI, p. 192-94 (which describes several thermostable liver preparations). Alternatively, the starting material may be fresh liver, frozen liver or a commercially-available liver preparation.

An acetone-insoluble fraction is separated from the starting material. This may be accomplished by admixing a large excess of acetone with the starting material which results in an acetone-insoluble fraction that is separated from the acetone. The treatment with acetone may be repeated. The acetone-insoluble fraction, after being separated from the acetone, is dissolved in water. Any remaining acetone is removed by, for example, distillation.

Alternatively, and preferably, before the acetone extraction, the starting material is dissolved in water with phenol. The solution is incubated at room temperature and after incubation, the solution is clarified by filtration, and the solution is passed over a cation exchange resin. The resulting resin-treated solution is then concentrated by evaporation, diluted with water, and centrifuged. The acetone-insoluble fraction is then separated from the supernatant by adding a large excess of acetone and further processed as described above.

The acetone-insoluble fraction may be further purified to remove the color pigments by treatment with activated charcoal. For example, the acetone-insoluble reaction may be dissolved in water and contacted with ammonia-activated charcoal.

A pharmaceutically-acceptable preservative usually is added to the water solution. For instance, phenol at from about 0.05 to about 1%, preferably about 0.5% may be added.

The liver extract useful in the present invention may be prepared according to the following examples.

EXAMPLE 1

Preparation of Liver Extract

Liver Fraction I, described in National Formulary XI, page 193, was dissolved in water to a concentration of 16% by weight. Phenol was added to a final concentration of 1%. The solution was mixed and incubated for seven days at room temperature. It was then clarified by filtration, and diluted to 8% solids by weight in water.

This aqueous solution was then passed three times through a cation exchange resin (sulfonated polystyrene). The resin-treated solution was clarified by filtration and concentrated to 40% total solids by weight by evaporation under vacuum at 65°-70° C. Cold water (5°-10° C.) was added (five volumes of water to seven volumes of liver solution) with mixing. The resultant solution was then centrifuged and the supernatant collected (Sharples-type centrifuge at 1 liter per minute). Phenol was added to a final concentration 0.5-1%.

The solution was adjusted to pH 6.0-7.0, with HCl or NaOH as necessary, clarified by filtration, and heated to 40° C. Then acetone was added (20-30 liters acetone per liter liver solution). The acetone-precipitable material was allowed to settle and most of the acetone was decanted off. The remaining suspension was incubated overnight at room temperature, after which the suspension was diluted to 10 liters with water, and the acetone was removed by distillation. Phenol and water were then added to give a final preparation containing 0.5% phenol and greater than 25 mg total solids per ml (herein designated "KU 10,000").

KU 10,000 was adjusted to pH 6.0-7.0 with HCl or NaOH, as necessary and diluted to 25 mg total solids per ml. with water (i.e., 2.5% by weight solids). The solution was then sterile filtered in suitable vials for use. This final solution is referred to herein as "KU 10,001".

EXAMPLE II

Physically Active Polypeptide Separation

A large excess of acetone "1800 ml" was added to eight vials KU 10,001 prepared according to Example I, 20 ml/vial, total of 160 ml, and left to stand at room temperature for four hours. After the precipitate settle down at the bottom of the beaker, the clear acetone layer decanted and the remaining suspension centrifuged for five minutes at 3000 RPM. The pellet then dissolved in 160 ml of water and freeze dried to produce about 4.0 g of dry powder consists of 0.3 mg protein/1 mg of dry powder weight. These samples were designated KU 10,172, KU 10,185, KU 10,211, KU 10,244 and KU 10,275

One gram of the dry powder was taken in 7 ml of 50 mM phosphate buffer, pH 7.5 and passed through a 100×2.5 cm column packed with Sephadex G50 suitable for use as a molecular sieve that exclude (does not retard) molecules with a molecular weight greater than 30,000 or BIOGEL p10 which exclude molecules with a molecular weight greater than 20,000. The column was equilibrated with 50 mM phosphate buffer before use at flow rate of 36 ml/hr. The column was eluted with 50 mM phosphate buffer pH 7.5. Seven ml. fractions were collected, and read at A280. Fractions were tested for angiotensin converting enzyme inhibition (using Furylacryloylphenylalanylglycylglycine as substrate) as described by Bush, Henry and Slasarchyk; *J. of Antibiotics* 37(4), 330 (1984). All fractions eluted before angiotensin converting enzyme inhibition were pooled according to the following table.

TABLE 1

| Loaded KU # | KU # | Pool # | Tube # |
|---|---|---|---|
| 10,244 | 10,245 | 1 | 22-30 |
|  | 10,246 | 2 | 31-50 |
| 10,185 | 10,190 | 1 | 14-16 |
|  | 10,191 | 2 | 18-20 |
|  | 10,192 | 3 | 21-23 |
|  | 10,193 | 4 | 26-29 |
| 10,275 | 10,275-I | 1 | 35-46 |
|  | 10,275-II | 2 | 47-58 |
|  | 10,275-III | 3 | 59-68 |

All pooled samples were concentrated, dialyzed in cellulose dialysis tubing with a molecular weight cut off of 1,000 and lyophilized.

EXAMPLE III

Further Purification of Physically Active Polypeptide

One gram of the dry powder KU#10,275 was dissolved in 7 ml of 50 mM phosphate buffer, pH 7.5 loaded on a 100×2.5 cm Bio-Gel P10 (Bio-Rad, Co.) suitable for use as a molecular sieve that exclude (does not retard) molecules with a molecular weight greater than 20,000 dalton. The column was equilibrated with 50 mM phosphate buffer pH 7.5. Seven ml fractions were collected, and read at A280. Fractions were tested for Angiotensin Converting Enzyme (ACE) inhibition (using furylacryloylphenylalanylglycylglycine as substrate) as described by Bush, Henry and Slasarchyk; *J. of Antibiotics* 37(4), 330 (1984). All fractions eluted before ACE inhibition were pooled according to the following table:

| Loaded KU # | KU #     | Pool # | Tube # | M. Wt  |
|-------------|----------|--------|--------|--------|
| 10,275      | 10,276-0 | 1      | 30-34  | 60,000 |
|             | 10,276-1 | 2      | 35-46  | 16,000 |
|             | 10,276-2 | 3      | 47-58  | 12,500 |
|             | 10,276-3 | 4      | 59-68  | 7,700  |

All pooled sample were concentrated, dialyzed in cellulose dialysis tubing with molecular weight cut off 1,000 and lyophilized, were tested for antiviral activity as in Example IV.

KU#10,276-0 was loaded over Anion Exchange Gel DEAE (diethylaminoethyl) exchange group by Bio-Rad packed in waters AP1 column (10×1 cm), eluted with buffer A: 20 mM potassium phosphate pH 8, B: 0.5M sodium chloride, gradient run at 214 nm, programmed: zero-100% B in 20 min. followed by 100% B for 10 min. and 100-zero % B in 1 min. Three fractions were collected, dialyzed and lyophilized. Fraction #3 was given KU#10,284. Antiviral activity tested as in Example IV. The results are shown in FIG. 6.

EXAMPLE IV

In Vitro Testing

Polypeptides prepared according to Example II were tested using the microtiter infection assay system described in *Journal of Clinical microbiology*, p. 231-235, Feb. 1968. Briefly, 100 microliters of KU 10,001 in growth medium (RPMI 1640 containing 16% fetal calf serum and 50 μg gentamicin per cl.) at various concentrations were added to the wells of a microtiter plate. MT-2 cells in 100 microliters of growth medium were added to give $3-4 \times 10^4$ cells per well. The plates were inacubated for 4 hours at 36° C. in 5% $CO_2$ in air and 100% humidity. Then 50 microliters of HIV-1 virus containing $5-25 \times 10^4$ infectious particles were added to each well. The plates were incubated 3-5 days at 36° C. in 5% $CO_2$ in air and 100% humidity. The MT-2 lymphoblastoid cell line is a human T-cell lymphotropic virus I-transformed T4+ T-lymphoblastoid cell line.

To assess culture viability and efficacy of treatment, 100 microliters of each test culture were then transferred by poly-L-lysine-coated wells in a new microtiter plate, and 100 microliters of 0.014% Finter neutral red in growth medium was added to each well. The plates wre incubated for 1 hour at 36° C., at which time the medium was removed, and the adhered cells were washed twice with 150 microliters of phosphate buffered saline. The dye was extracted from the adhered cells by adding 100 microliters of acidified alcohol (50% ethanol in 1% acetic acid), and the absorbance of the extracted dye solution at 540 nm was measured.

The results of this assay are shown in FIGS. 6 which shows that the active peptide produced nearly 100% cell protection from the cytotoxic effects of HIV-1 after HIV-1 was added to cultures of MT-2 at approximately 8 μg/ml. Additionally, 50-60% activity was observed on the average at as little as 1.5 μg/ml. This is a significant improvement over KU-10,275 liver extract were 50% activity was observed at 100 μg/ml concentration of active peptide.

PHYSICALLY ACTIVE POLYPEPTIDE SEPARATION

KU 10,172 prepared according to Example II was fractionated on reverse phase $C_{18}$ prep column, eluted with buffer A: 20 mM ammonium acetate pH 7.0, B: 80% acetonitrite in buffer A, gradient run at 214 nm, programmed: zero to 80% B in 80 min. at 8.4 ml/min. Fractions collected 8.4 ml/test tube. All tubes were analyzed by analytical $C_{18}$ reverse phase column and size exclusion high pressure liquid chromatography column Tsk 125 and pooled to twelve fractions based on its retention times. Eight fractions KU 10,201 to KU 10,208 were tested for anti-viral activity and showed a significant cell protection activity.

FURTHER PURIFICATION OF PHYSICALLY ACTIVE POLYPEPTIDE

KU 10,203 and KU 10,207 prepared according to Example IV were further purified on reverse phase $C_{18}$ prep column, eluted with buffer A: 20 mM ammonium actuate pH 7.0, B: 80% acentonitrite in buffer A, gradient run at 214 nm, programmed: Zero to 80% B in 80 min, at 8.4 ml/min. Fractions collected 8.4 ml test tube. All tubes were analyzed by analytical $C_{18}$ reverse phase column and size exclusion high pressure liquid chromatography column (Tsk 125) and pooled according to its retention times to produce KU 10,214 and KU,215. The cDNA from rat liver for the KU 10,214 and KU 10,215 fractions that were active in the bioassay was isolated and cloned using the polymerase chain reaction technique. The desired sequence to be amplified was that of the gene in pig liver cells that encodes the peptides in the KU 10,214 and KU 10,215 fractions.

ACTIVE FRACTION PEPTIDE AMINO TERMINAL AMINO ACID SEQUENCING

Ten amino acids of amino terminal sequence of KU 10,214 and KU 10,215 were determined by Edman degradation using an Applied Biosystems model 477A automated peptide sequencer with attached High Pressure Liquid Chromatography model 120A on-line phenyl isothiocyanate analyzer found to be (Ala or Val or Ile) Glu (His or Pro) Gly (Tyr or Met or Thr) His Gly Pro His Gly. (Sequence Id. No. 10) More specifically, KU 10,214 has the amino acid sequence:
(Ala or Val or Ile) - (Glu or Gln) - (His or Pro or Arg) - Gly - Thr - His - Xaa - pro - His - Gly. (Sequence Id. No. 11)

KU 10,215 has the amino acid sequence:
(Ala or val or Ile) - (Glu or Gln) - (His or Pro) - Gly - (Tyr or Met) - His - Gly - Xaa - His - Gly - Xaa - Xaa - Gly -Xaa- Gln. (Sequence Id. No. 12)

Due to the similarity of both sequences, we proposed a sequence to be used for our Polymerase Chain Reaction (PCR) work using the following deca peptide sequence. Ala - Glu - His - Gly - Tyr - His - Gly - Pro - His - Gly. (Sequence Id. No. 13).

POLYMERASE CHAIN REACTION PRIMER DESIGN

The oligonucleotide primer 5'CATGGICCICATG-GI3'[I indicates Inosine] (Sequence Id. No. 14) was designed based on the five amino acid sequence (HGPHG) region sequence that was common to both the KU 10,214 and KU 10,215 fractions active in the bioassay. This primer corresponds to the indicated amino acids regardless of codon usage except for His. Codon bias analysis for all pig gene sequences found in the databank Genbank 66 showed His codon at CAT to be used about 2.5 time as often as His codon CAC. This and the rarity of CG dinucleotides in peptide coding regions of mammalian genomes (Sambrook, J., Fritsch, E. F. and Maniatis, T. (1989) in "Molecular Cloning: A Laboratory Manual", 2nd edition, Cold Spring Harbor Laboratory, Cold Spring Harbor, N.Y.) dictated use of CAT and not CAC for His in this sequence producing a primer sequence of 5'CATGGICCICATGGI 3'. (Sequence Id. No. 14) This primer was prepared by conventional techniques using an Applied Biosystems DNA synthesizer. See FIGS. 1A and 1B.

RNA ISOLATION

Total RNA (2.5 mg) was isolated from 1.5 grams of fresh liver tissue from a female pig by rapid homogenation in guanidine thiocyanate followed by extraction with phenol (Chomczynski, P. and Sacchi, N. (1987) Anal. Biochem 162, 156–159). After two successive precipitations with isopropanol, the purified RNA was dissolved in water. The RNA was then subjected to poly(U) Sepharose chromatography, (Jacobson, A. (1987) Meth. Enzymology 152, 254–261), which yielded 21 µg of Poly(A)+RNA from 1 mg of total RNA.

CDNA SYNTHESIS AND INTERMEDIATE POLYMERASE CHAIN REACTION AMPLIFICATION

Double stranded cDNA was prepared from the Poly-(A)+RNA by a modification of the method of Gubler and Hoffman (Gene 25, 283 (1983)). Five µg of Poly-(A)+RNA was used with an oligo(dT)-Hind III primer and AMV reverse transcriptase to synthesize the first strand, and second strand conversion was accomplished using RNase H and E. Coli DNA polymerase I. The yield was 30% first strand conversion and 100% second strand conversion. The double stranded cDNA was extracted with phenol and precipitated with ethanol by conventional methods. After treatment with T4 DNA polymerase to flush the ends, the cDNA was ligated with UNIAMP adaptors (Clontech Labs Inc. 800-662-CLON) under conditions described by the manufacturer. Following ligation, 3 µl of a 1:10 dilution of the cDNA was amplified by polymerase chain reaction in the Perkin Elmer Cetus GENEAMP System using a single UNIAMP primer (Clontech) under conditions described by the manufacturer. A sample of the reaction products was analyzed by agarose gel electrophoresis in the presence of ethidium bromide. The results showed a distribution of cDNA products that closely matched the pattern of unamplified cDNA. The remainder of the reaction products were purified by extraction with phenol and SEPHAROSE (Pharmacia Co.) CL-4B chromatography. These intermediate amplification and purification steps produced a sufficient amount of pure cDNA free of extraneous sequences which could have interfered with subsequent procedures.

POLYMERASE CHAIN REACTION AMPLIFICATION WITH THE SPECIFIC PRIMER

The amplified cDNA was precipitated with ethanol, collected by centrifugation and dissolved in 20 µl water. A 1 µl sample was used for polymerase chain reaction amplification with the specific primer described above in combination with oligo (dT)-Hind III primer. Conditions for polymerase chain reaction were 30 cycles at 94° C. for one minute, and 72° C. for two minutes per cycle, with a final extension at 72° C. for five minutes. A fraction of the reaction products were analyzed by agarose gel electrophoresis in the presence of ethidium bromide. The results showed three major DNA species in the range of 200 base pairs, 400 base pairs and 500 base pairs. Control reactions in which the primers were omitted produced no detectable products. The strategy for sequencing this DNA is shown in FIGS. 2A and 2B.

CLONING OF THE POLYMERASE CHAIN REACTION PRODUCTS

The remainder of the polymerase chain reaction products was treated with T4 DNA polymerase to flush the ends, and then purified by phenol extraction and ethanol precipitation. The DNA was ligated with ECOR I linkers under standard conditions. Following digestion with ECO RI and Hind III and removal of small molecules by SEPHAROSE (Pharmacia Co.) CL-4B chromatography, the prepared DNA was ligated with ECO RI/Hind III EXLOX vector arms, packaged in vitro, and plated on E. Coli by standard methods. The resulting library contained $3 \times 10^5$ independent clones and was amplified to a titer of $3 \times 10^{10}$ pfµ/ml.

VERIFICATION OF CLONING

The library was plated at a density corresponding to approximately 1,000 plaques per 82 mm plate. Plaque lifts were prepared and hybridized with random-primer labeled DNA probes by conventional methods. Using a probe from DNA amplified with the specific primer described above, virtually every plaque produced a positive hybridization signal. This indicated the library contained the desired inserts of polymerase chain reaction products.

DNA SEQUENCING

Six randomly chosen plaques were converted to plasmid subclones for DNA sequence analysis. Restriction enzyme analysis showed an insert of approximately 500 base pairs in four of these isolates. Plasmid DNA was prepared and sequenced directly using T7 DNA polymerase (promega) and chain-terminating dideoxynucleotides (Mierendorf, R. C. and Pfeffer, D. (1987) Meth. Enzymol. 152, 556–562).

DNA SEQUENCING

Sequencing experiments determined 96 base pairs at the 5' end and 110 pairs at the 3' of the cDNA insert, which appeared to be identical in the clones sequenced.

The 5' 96 base pairs encoded a 32 amino acid polypeptide (Sequence Id. No. 1) whose first four amino acids GPHG corresponded to those of the primer HPGHG.(Sequence Id. No. 2) The 110 pairs at the 3' end (Sequence Id. No. 3) had a TAA or ATG stop codon in all three reading frames, so the C-terminal of the polypeptide is L (encoded by 5'CTA3'), (Sequence Id. No. 4 which has 8 amino acids and is encoded by (Sequence Id. No. 5) and/or (Sequence Id. No. 6) which has 21 amino acids and is encoded by Sequence Id. No. 7. As such the polypeptides are characterized by the Sequence Id. No. 1 at the 5' end and Sequence Id. Nos. 4 and 6.

FURTHER PURIFICATION OF PHYSICALLY ACTIVE POLYPEPTIDE

KU10,275 was run over large G-50 (Pharmacia, Co) column desalted with Amicon filter (MW cut off 3500), lyophilized and protein content and molecular weight were determined. The molecular weight was determined to be approximately 10,000 and protein content was 72 percent. The new designation for this peptide is KU10,280.

PHYSICAL AND CHEMICAL TESTS ON PHYSIOLOGICALLY ACTIVE POLYPEPTIDE

Thus, the physiologically-active polypeptide may be characterized by its physical and chemical properties. The active polypeptide is insoluble in acetone, and soluble in water. It has a molecular weight as determined by molecular sieve chromatography experiments to be about 5,000–40,000.

ADMINISTRATION OF POLYPEPTIDES

The polypeptides useful in the present invention preferably are administered by injection, for example, intramuscular injection. However, other forms of administration are contemplated. The polypeptides may be employed in the form of pharmaceutically-acceptable salts of the components, such as the alkali metal salts. The pharmaceutically-acceptable amides, lower alkyl esters, protected derivatives, other derivatives and analogues of the components of the polypeptides are also contemplated.

Although, as indicated, the polypeptides may be used as a water solution, it may also be utilized in association with other pharmaceutical carriers, for example, in saline solution. In any case, since the polypeptide is preferably administered by injection, it is contemplated that the extract will be contained in a water base carrier. A preferred product is a polypeptide water solution containing about 2.5% by weight of polypeptide. More generally, the polypeptide ranges from 5 µg to 500 µg per ml of carrier.

ADMINISTRATION OF LIVER EXTRACT

The acetone-insoluble liver extract useful in the present invention preferably is administered by injection, for example, intramuscular injection. However, other forms of administration are contemplated.

The liver extract may be employed in the form of pharmaceutically-acceptable salts of the components, such as the alkali metal salts. The pharmaceutically-acceptable amides, lower alkyl esters, protected derivatives, other derivatives and analogues of the components of the liver extract are also contemplated.

Although, as indicated, the liver extract may be used as a water solution, it may also be utilized in association with other pharmaceutical carriers, or example, in saline solution. In any case, since the liver extract is preferably administered by injection, it is contemplated that the extract will be contained in a water base carrier. A preferred product is a water solution containing about 2.5% by weight of liver extract solids.

Dosages may vary depending upon the condition of the patient. Generally, however, it has been found that the administration of 2 ml. of KU 10,001 prepared as described in Example 1 intramuscularly every other day will produce beneficial results in as little as about 4 weeks.

EXAMPLE 1

Figure 4:
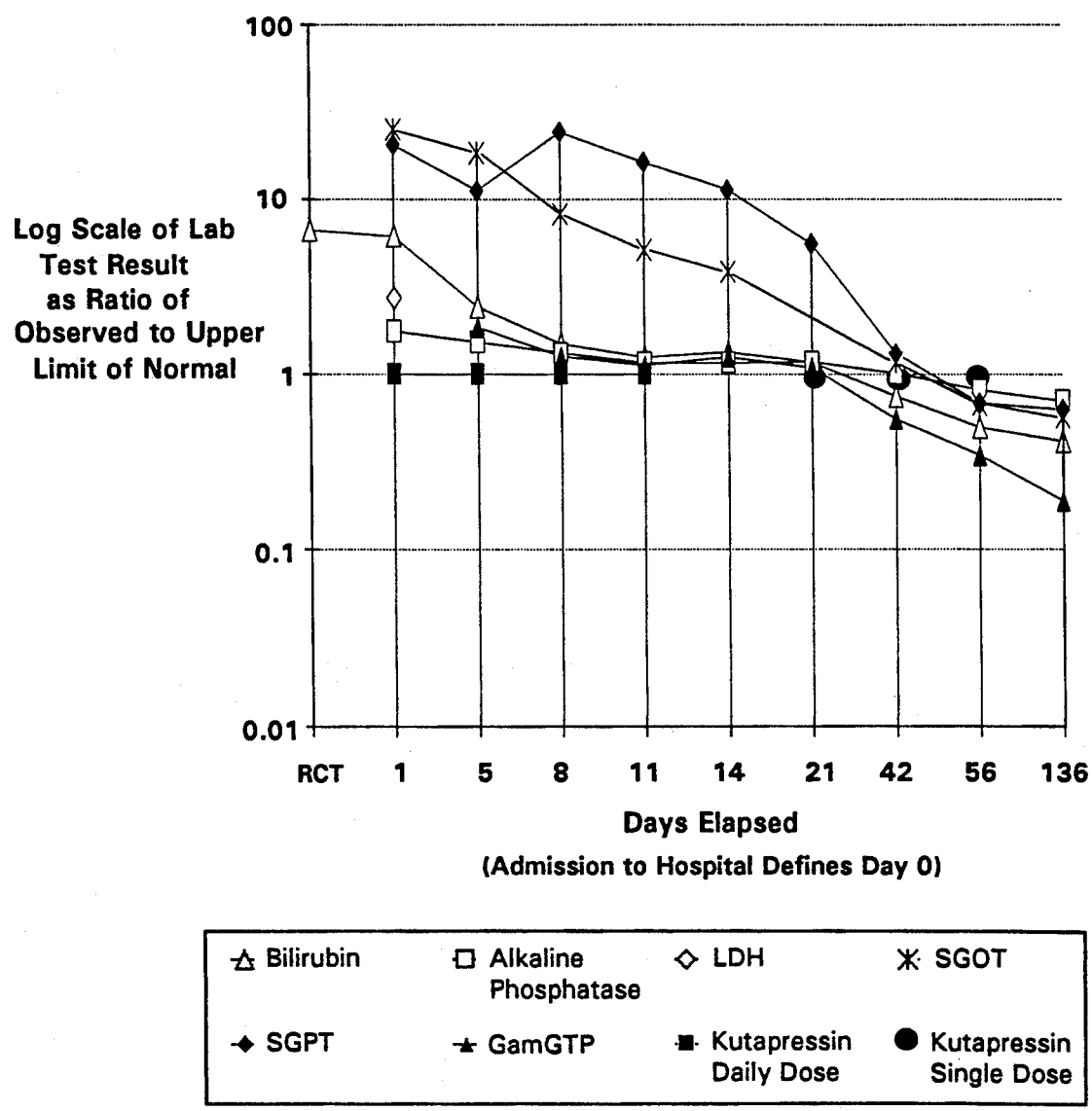
FIG. 4 shows acute hepatitis B patient number 2's liver function data charted during and after administration of KUTAPRESSIN (Kremers-Urban Co.).

Acute hepatitis B patients No. 1 and 2 received 2 cc's of KUTAPRESSIN (Kremers-Urban Co.) intramuscularly daily. These injections were begun after admission to the hospital. Certain blood chemistries were monitored on a daily basis. These include total bilirubin (Bili(total) alkaline phosphatase (ALK Phos) Lactate-D-dehydrogenase (LDH), Serum glutamicpyruvic transaminase (SGOT) and Serum Glutamic oxalacetic transaminase (SGPT). In an acute hepatitis B infection one would expect a rate of recovery of about two months for the liver. In contrast, to what is normally observed, the attending physician observed a decrease in SGOT values to a normal value (as shown by the line at numeral 1.0) in only 28 days for patient 1 (see FIG. 3) and 46 days (see FIG. 4). The normal value is shown by the horizontal line labelled 1.

EXAMPLE 2

Solutions of active peptide obtained according to the previous disclosure were tested for antihepatitis viral activity at four concentrations: 100, 10, 1.0, and 0.1 µg/ml. Compounds were tested for toxicity starting at 1000 µg/ml.

Details of the assay methodology can be found in: Korba and Milman, *Antiviral Res.*, 15:217 (1991) and Korba and Gerin, *Antiviral Res.* (1992) (in press). The antiviral evaluations were performed on two separate passages of cells. All wells, in all plates, were seeded at the same density and at the same time. Due to the inherent variations in the levels of both intracellular and extracellular HBV DNA, only depressions greater than 3.5-fold (for HBV virion DNA) or 3.0-fold (for HBV DNA replication intermediates) from the average levels for these HBV DNA forms in untreated cells are generally considered to be statistically significant [$P<0.05$]. The levels of integrated HBV DNA in each cellular DNA preparation (which remain constant on a per cell basis in these experiments) were used to calculate the levels of intracellular HBV DNA forms, thereby eliminating technical variations inherent in the blot hybridization assays.

Typical values for extracellular HBV virion DNA in untreated cells range from 50 to 100 pg/ml culture medium (average of approximately 76 pg/ml). Intracellular HBV DNA replication intermediates in untreated cells range from 50 to 100 pg/µg cell DNA) (average approximately 74 pg/µg cell DNA). In general, depressions in the levels of intracellular HBV DNA due to treatment with antiviral compounds are less pronounced, and occur more slowly, than depressions in the levels of HBV virion DNA).

For reference, the manner in which the hybridization analyses were performed for these experiments results in an equivalence of approximately 1.0 pg intracellular HBV DNA/µg cellular DNA to 2-3 genomic copies per cell and 1.0 pg of extracellular HBV DNA/ml culture medium to $3 \times 10^3$ viral particles/ml.

Toxicity analyses were performed in order to assess whether any observed antiviral effects are due to a general effect on cell viability. The method used was uptake of neutral red dye, a standard and widely used assay for cell viability in a variety of virus-host systems, including HSV and HIV.

ANTIVIRAL EVALUATIONS

Controls

Within normal variations, levels of HBV virion DNA and intracellular HBV replication intermediates (HBV RI) remained constant in the untreated cells over the challenge period. The positive treatment control, 2,3'-dideoxycytosine (2'3'-ddC), induced significant depressions of HBV DNA replication at the concentration used. At 9 µM 2'3-ddC, a 90% depression of HBV RI (relative to average levels in untreated cells) is typically observed in this assay system.

Test Compounds

Figure 5A:
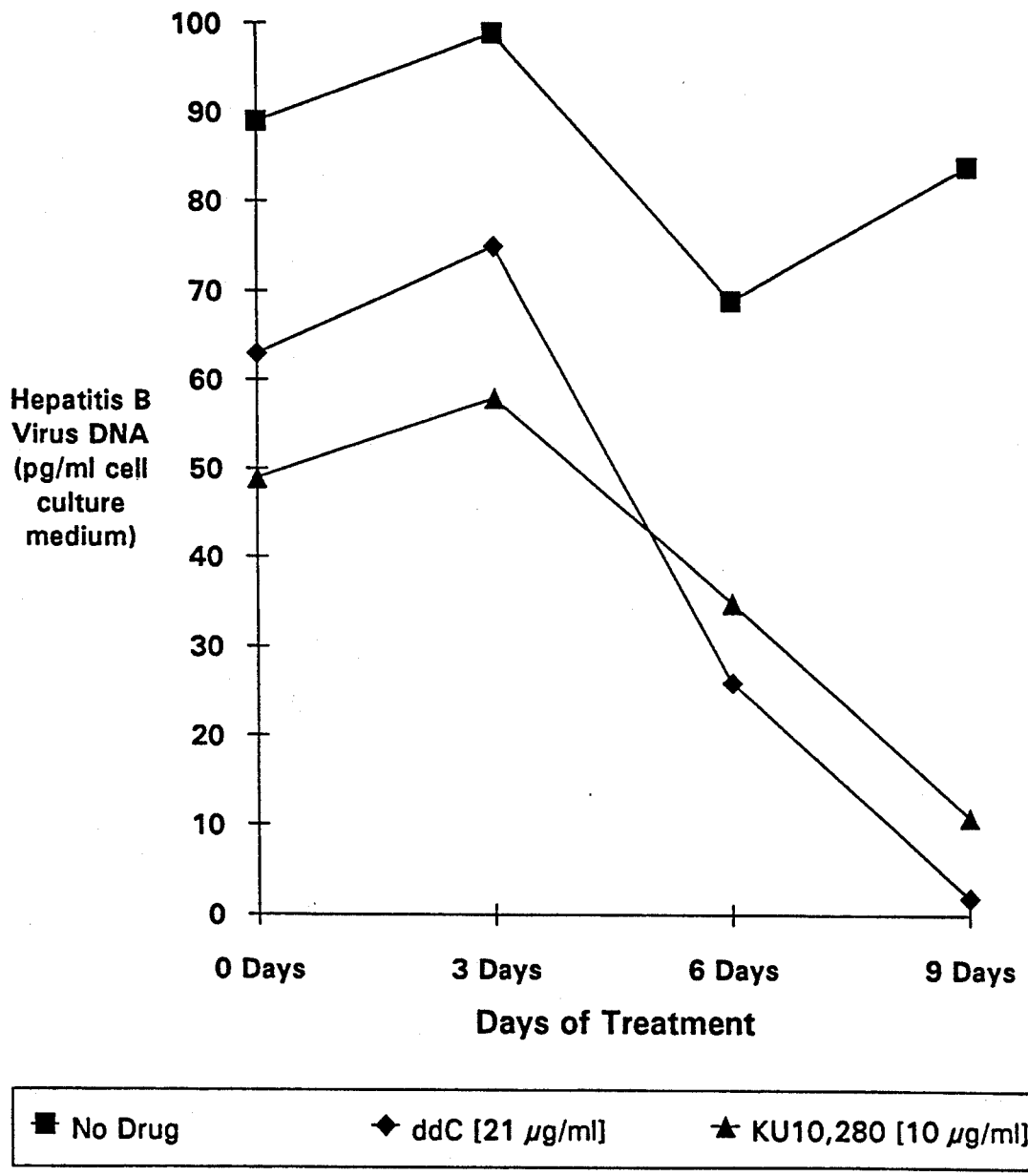
FIG. 5A shows anti-virus effect of 10 $\mu$g/ml of active peptide compared to 2.1 $\mu$g/ml 2,3'-dideoxycytosine.
Figure 5C:
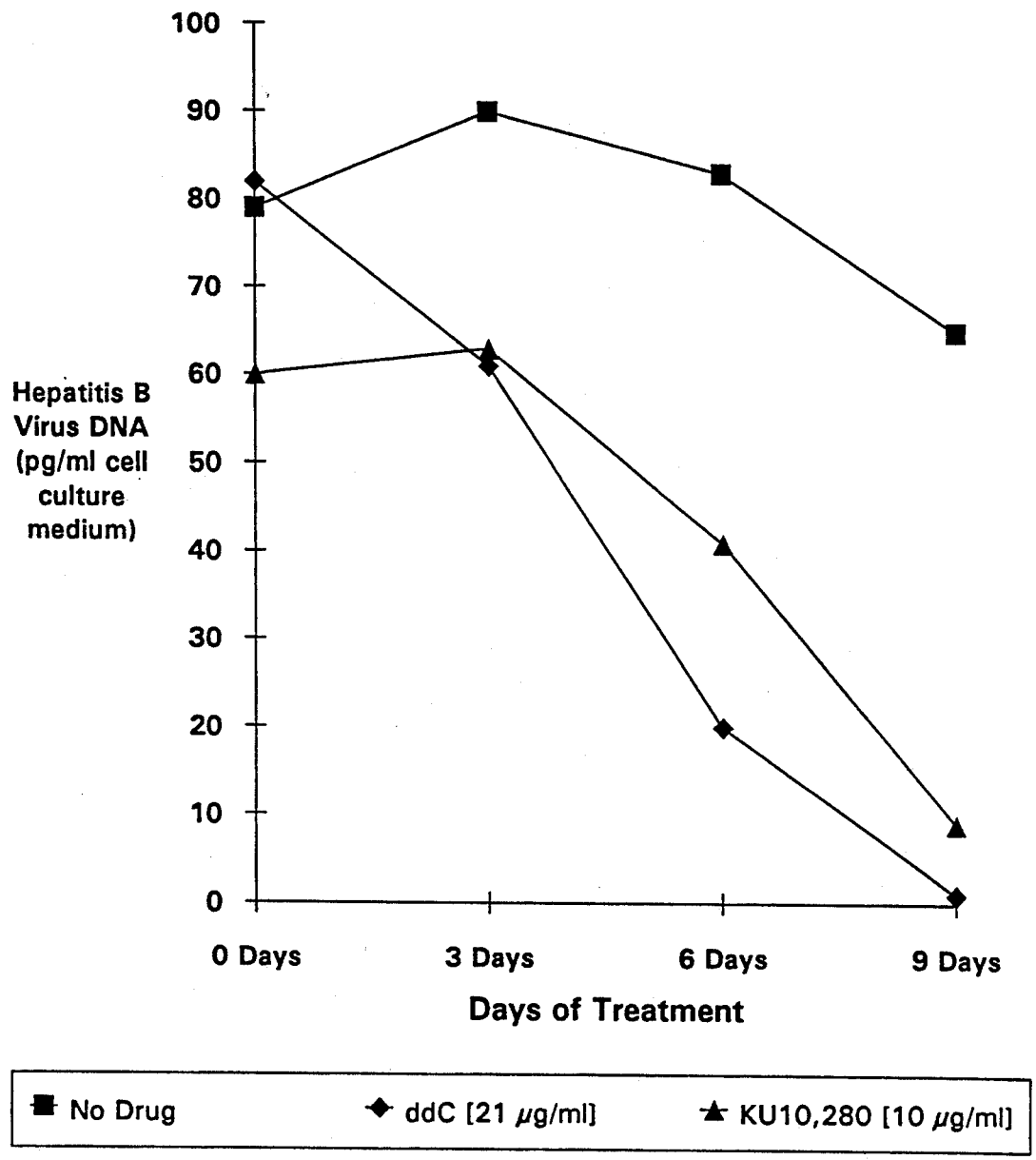
FIG. 5C shows anti-virus effect of 10 $\mu$g/ml of active peptide compared to 2.1 $\mu$g/ml 2,3'-dideoxycytosine.
Figure 5D:
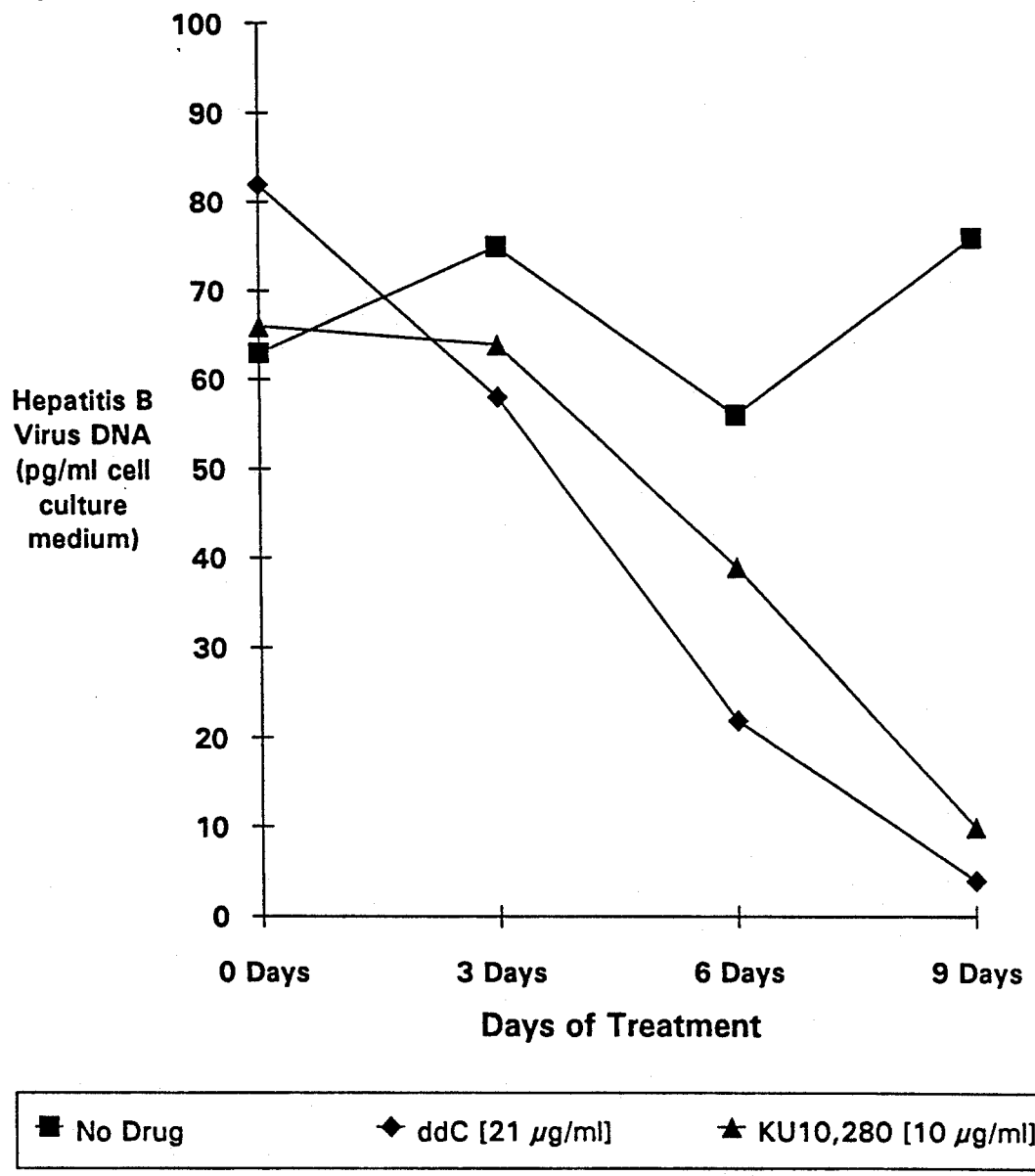
FIG. 5D shows anti-virus effect of 10 $\mu$g/ml of active peptide compared to 2.1 $\mu$g/ml 2,3'-dideoxycytosine.

The active peptide solutions were found to be moderate inhibitors of intracellular HBV replication. HBV virion DNA and HBV RI were depressed to a degree comparable to, but generally less than, that observed following treatment with 2'3'-ddC. However, the active peptide solutions (10 μM) were observed to provide six to eight fold reduction in HBV viron extracellular DNA at nine days. See FIG. 5 and Table II.

In the following data table, data is shown concerning analysis of intracellular HBV DNA at 24 hours following the 9th day of treatment. DNA in each cell DNA preparation were used to calculate the levels of episomal 3.2 Kb HBV genomes (MONO.) and HBV DNA replication intermediates (RI). A "zero" indicates an undetectable level of HBV DNA, sensitivity cutoff was 0.1 pg/ml.

ses were cultured and treated with test compounds with the same schedule as used for the antiviral evaluations. Each compound was tested at four concentrations, each in triplicate cultures. Uptake of neutral red dye was used to determine the relative level of toxicity. The absorbance of internalized dye at 510 nM ($A_{510}$) was used for the quantitative analysis. Values are presented as a percentage of the average $A_{510}$ values (±standard deviations) in nine separate cultures of untreated cells maintained on the same 96-well plate as the test compounds. The percentage of dye uptake in the nine control cultures on plate 35 was 100±4.

TABLE III

| COMPOUND | Neutral Red Dye Uptake at Indicated Drug Concentration (% of Control) | | | |
|---|---|---|---|---|
| | 1000 μg/ml | 3000 μg/ml | 10 μg/ml | 30 μg/ml |
| 2'3'-ddC | 12 ± 5 | 40 ± 4 | 102 ± 2 | 101 ± 3 |
| KU 10,280 | 45 ± 8 | 76 ± 4 | 103 ± 3 | 103 ± 1 |
| KU 10,284 | 49 ± 1 | 73 ± 4 | 103 ± 2 | 102 ± 2 |

TABLE II

| TREATMENT | Intracellular HBV DNA @ (pg/μg CELL DNA) | | HBV VIRION DNA # (pg/ml CULTURE MEDIUM) | | | |
|---|---|---|---|---|---|---|
| | MONO. | RI | DAY 0 | DAY 3 | DAY 6 | DAY 9 |
| UNTREATED CELLS | 2.7 | 70 | 89 | 99 | 69 | 84 |
| " | 2.9 | 96 | 87 | 63 | 77 | 60 |
| " | 2.5 | 51 | 79 | 90 | 83 | 65 |
| " | 2.7 | 73 | 63 | 75 | 56 | 76 |
| 2',3'-ddC @ 10 μM | 1.6 | 7 | 63 | 75 | 26 | 2 |
| " | 1.8 | 9 | 87 | 56 | 21 | 1 |
| " | 1.8 | 4 | 82 | 61 | 20 | 1 |
| KU 10,280 @ 100 μg/ml | 1.8 | 2 | 51 | 52 | 21 | 1 |
| " | 2.2 | 3 | 60 | 42 | 26 | 0 |
| " | 2.0 | 1 | 75 | 56 | 21 | 0 |
| " | 1.9 | 2 | 88 | 70 | 20 | 1 |
| KU 10,280 @ 10 μg/ml | 2.1 | 13 | 49 | 58 | 35 | 11 |
| " | 2.5 | 10 | 78 | 69 | 33 | 7 |
| " | 2.7 | 11 | 60 | 63 | 41 | 9 |
| " | 2.3 | 12 | 66 | 64 | 39 | 10 |
| KU 10,280 @ 1.0 μg/ml | 2.6 | 65 | 52 | 44 | 56 | 93 |
| " | 2.2 | 66 | 53 | 50 | 53 | 71 |
| " | 2.1 | 54 | 58 | 57 | 64 | 72 |
| " | 2.4 | 50 | 73 | 70 | 99 | 75 |
| KU 10,280 @ 0.1 μg/ml | 2.5 | 51 | 79 | 52 | 42 | 65 |
| " | 2.2 | 53 | 89 | 81 | 51 | 70 |
| " | 2.7 | 66 | 61 | 53 | 72 | 80 |
| " | 2.5 | 62 | 64 | 70 | 57 | 91 |
| KU 10,284 @ 100 μg/ml | 1.7 | 16 | 48 | 63 | 36 | 10 |
| " | 1.9 | 15 | 80 | 60 | 36 | 12 |
| " | 1.8 | 17 | 68 | 81 | 33 | 13 |
| " | 2.2 | 12 | 50 | 67 | 30 | 9 |
| KU 10,284 @ 10 μg/ml | 2.8 | 44 | 55 | 47 | 68 | 23 |
| " | 2.7 | 38 | 61 | 56 | 64 | 25 |
| " | 2.0 | 47 | 70 | 51 | 69 | 22 |
| " | 2.0 | 39 | 70 | 78 | 65 | 26 |
| KU 10,284 @ 1.0 μg/ml | 2.6 | 53 | 78 | 78 | 67 | 90 |
| " | 2.2 | 64 | 64 | 77 | 77 | 78 |
| " | 2.3 | 68 | 83 | 81 | 67 | 54 |
| " | 2.4 | 75 | 55 | 81 | 86 | 68 |
| KU 10,284 @ 0.1 μg/ml | 2.5 | 58 | 53 | 57 | 59 | 82 |
| " | 2.2 | 69 | 64 | 89 | 68 | 69 |
| " | 2.6 | 67 | 70 | 75 | 78 | 63 |
| " | 2.5 | 80 | 65 | 80 | 58 | 92 |

TOXICITY EVALUATIONS

No significant toxicity (greater than 50% depression of the dye uptake levels observed in untreated cells) was observed for the test compounds at the concentrations used for the antiviral evaluations. Significant toxicity was observed for both test compounds at the highest concentrations used in the toxicity evaluations.

Toxicity results were performed in 96-well flat bottomed tissue cultures plates. Cells for the toxicity analy- In summary, a six to eight fold reduction in HBV Viron extracellular DNA at nine days with an active peptide solution at 10 μM was observed. This concentration was shown to be nontoxic in the dye uptake assay. This data suggests that the active peptide solution is nearly equipotent with 2', 3' ddc, but is less toxic.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

---

We claim:

1. A method of treating hepatitis B viral infection comprising:
administering to a mammal having hepatitis B infection a therapeutically effective amount of a mammalian liver extract referred to as KU 10,001, the extract being heat stable, insoluble in acetone and soluble in water.

2. The method of claim 1 wherein the liver extract is a porcine liver extract.

3. The method of claim 1 wherein the liver extract is contained in a pharmaceutically-acceptable carrier at a concentration of about 2.5% by weight solids.

4. The method of claim 2 wherein the liver extract is contained in a pharmaceutically-acceptable carrier at a concentration of about 2.5% by weight solids.

5. The method of claim 4 wherein the liver extract is contained in water.

* * * * *